United States Patent [19]

Taylor et al.

[11] Patent Number: 4,988,338
[45] Date of Patent: Jan. 29, 1991

[54] IDENTIFICATION ACCESSORY DEVICE

[76] Inventors: Kermit K. Taylor, 5354 Roxbury Rd., Indianapolis, Ind. 46226; Kermit L. Taylor, 16182 Rapids Rd., Burton, Ohio 44021

[21] Appl. No.: 267,368

[22] Filed: Nov. 4, 1988

[51] Int. Cl.5 ............................................. A61M 25/02
[52] U.S. Cl. ........................... 604/180; 128/DIG. 26; 248/205.2; 248/74.3
[58] Field of Search .................................. 604/174–180; 128/DIG. 15, DIG. 26; 269/328; 248/205.2, 74.3, 68.1; 24/306, 16 R, 442

[56] References Cited

U.S. PATENT DOCUMENTS

| | | | |
|---|---|---|---|
| 4,059,105 | 11/1977 | Cutruzzula et al. | 604/180 |
| 4,122,857 | 10/1978 | Haerr | 128/DIG. 26 |
| 4,457,754 | 7/1984 | Buttaravoli | 128/DIG. 26 |
| 4,484,914 | 11/1984 | Brown | 128/DIG. 26 |
| 4,606,735 | 8/1986 | Wilder et al. | 128/DIG. 26 |
| 4,665,566 | 5/1987 | Garrow | 128/DIG. 15 |
| 4,671,787 | 6/1987 | Widman | 128/DIG. 26 |
| 4,702,736 | 10/1987 | Kalt et al. | 128/DIG. 26 |
| 4,795,429 | 6/1989 | Feldstein | 604/174 |

Primary Examiner—John D. Yasko
Assistant Examiner—Anthony M. Gutowski
Attorney, Agent, or Firm—Robert A. Spray

[57] ABSTRACT

A body member provides a mounting panel for attachment pieces which provide an identification tag for respective ones of a plurality of service tubes or lines, and which, instead of merely identifying the tube by attaching to it, provide the double function of holding the tube to the mounting panel and identifying the tube; and the plurality of separate identification attachments, in the kit with the mounting panel, provide that the array of tubes are not only respectively identified but are easily mounted in an orderly arrangement on the mounting panel. Velcro (hook and loop type fastener material) material preferably is used on both the attachment pieces and the other surface of the panel member; and adhesive material is preferably used for the rear of the panel member, providing easy but removable attachment to any associated support.

7 Claims, 2 Drawing Sheets

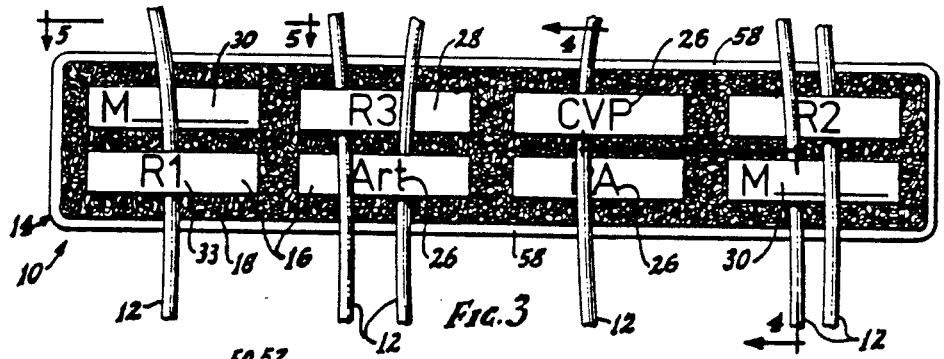
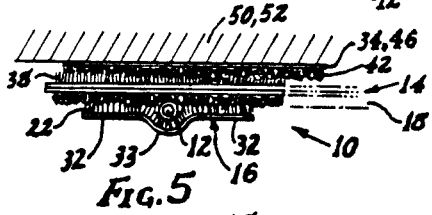
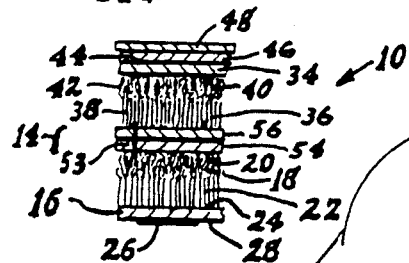
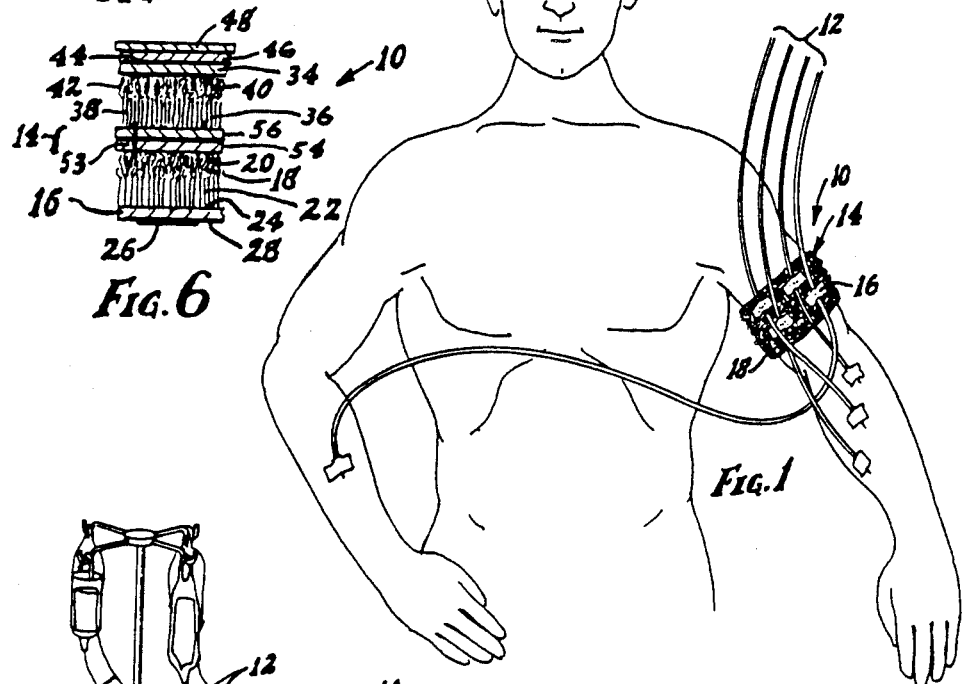
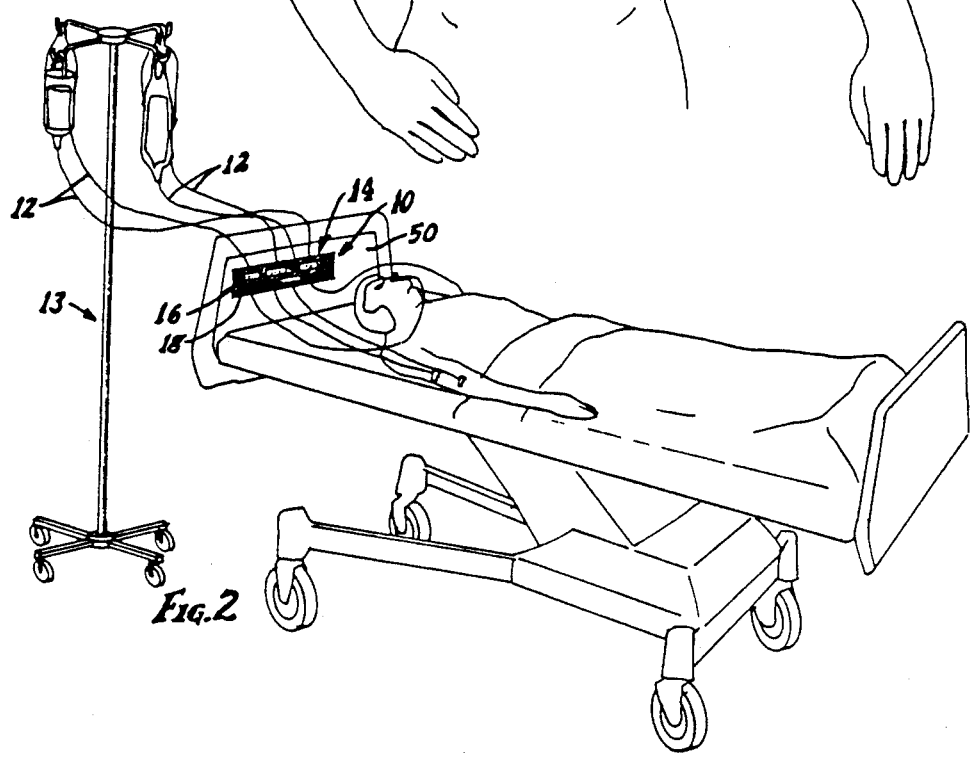

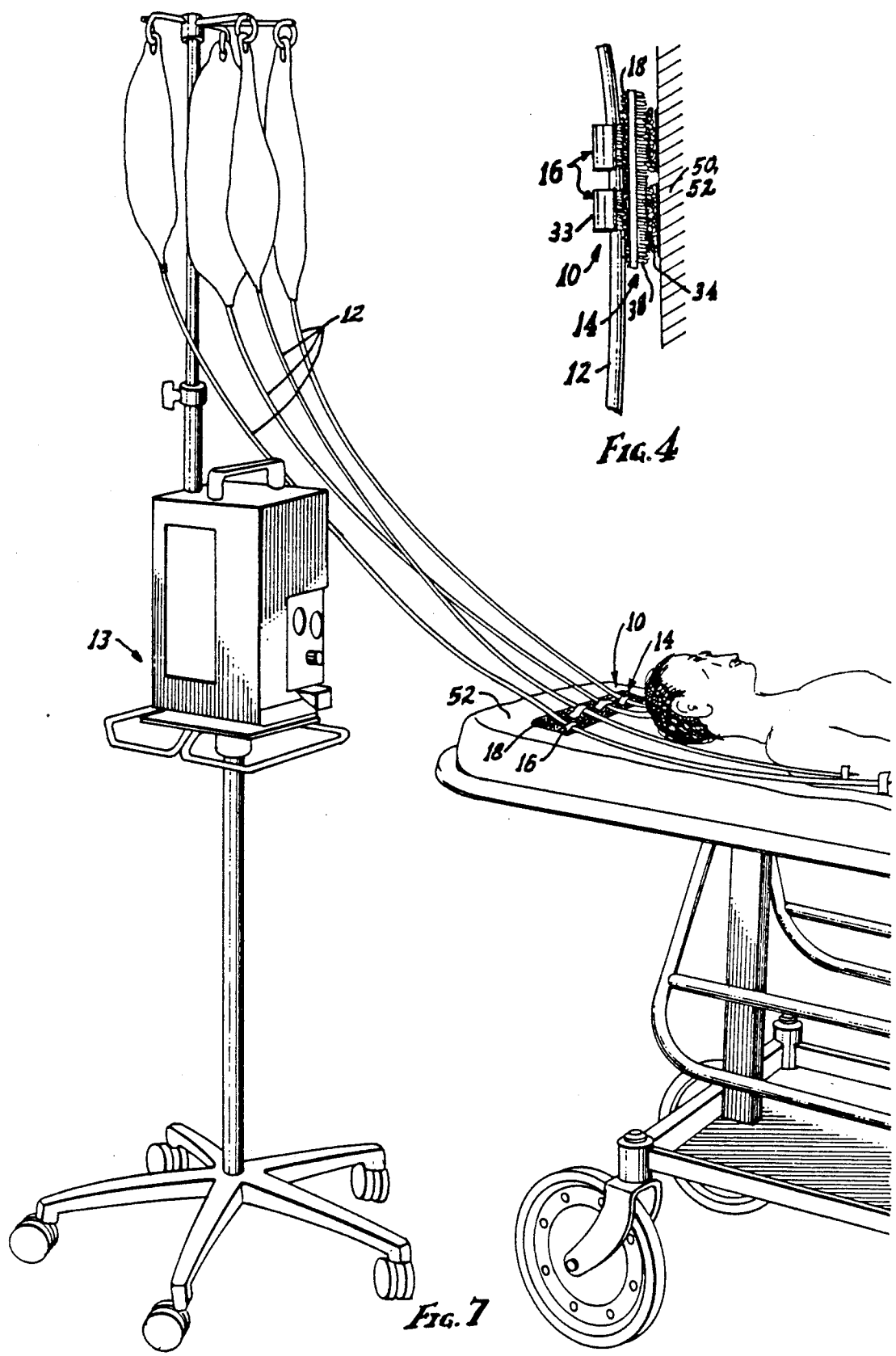

IDENTIFICATION ACCESSORY DEVICE

FIELD OF THE INVENTION

The present invention relates to work-situations such as especially medical therapy situations in which a plurality of servicing tubes or lines are necessarily in a close vicinity, such as being all attached to a patient or to equipment nearby the patient.

The tubes are generally of a similar size, shape, and color. Moreover, the somewhat-temporary nature of each such installation of one or more of the tubes makes it difficult to wholly avoid a disorderly and confusing array of group of tubes.

Further, the identification, orderliness, and relative location of individual tubes is often made difficult by their relatively close proximity and the smallness of work area serviced by a number of persons.

Thus, identification of all the array of tubes is difficult, even though often of critical importance as to accuracy and rapidity of identification, in spite of such problems of identification and general orderliness of the tube grouping.

Thus, more particularly, the present invention relates to work-situations in which identification of tubes or invention relates to work-situations in which identification of tubes or lines is of importance even though the assembly of service tubes or lines, or perhaps of an individual one or mores of them, is often of only a quite temporary nature.

Yet, in spite of the difficulties of such work situation, and in spite of often great stressfulness of the situation, accuracy and rapidity of identification is quite vital concern; and other methods do not give the advantages of the present invention.

SUMMARY OF THE INVENTION

The present invention builds upon the prior art, in providing in kit form a combination of a panel member and a plurality of attachment pieces or tags, with the preferred embodiment providing Velcro (hook and loop type fastener material) releasable attachability; and, with the various attachment tags bearing appropriate identification indicia, and in the form of small strap-like pieces, each attachment piece is pressed against the panel member and over a portion of a respective one of the service tubes or lines. (Velcro is believed to be a registered trademark having, as such, a function of denoting the source or distributor of hook and loop fastener material, but it also is indicative of such fastener sheets themselves as fastening means to establish and hold a releasable connection, and is so used herein in the latter sense.)

Thus, each attachment piece of the kit both identifies a service tube and effects its mounting onto the panel member; and the several attachment pieces co-operate with one another, and with each's respective service tube, and with the panel member, to achieve an orderly and releasably fixed array of the whole group of service tubes, each identified for easy and rapid identification.

THE INVENTION'S COMPONENTS AND CONCEPTS ARE SIMILAR TO THOSE AVAILABLE IN THE PRIOR ART, EXCEPT FOR THE PRESENT CONCEPTS IN PARTICULAR COMBINATION

In a hindsight consideration of the present invention to determined factors of its inventive and novel nature, it is also not only conceded but emphasized that the prior art had details usable in this invention if the prior art had had the guidance of the present invention's concepts.

That is, it is emphasized that the prior art had the following several particulars; however, and most significantly, the prior art had not had them in the advantageous and particular overall combinations achieving the overall effect provided by this invention as a whole:

a. The prior art had many sorts of mounting panels, for many years;

b. The prior art for many years has had many types of releasable fasteners, specifically including the Velcro type fasteners here preferred for attaching the identification tags to the outer surface of the body member which serves as a mounting panel, and adhesive fasteners such as here preferred for attaching the body member mount to an associated component;

c. The prior art for many years has had identification tags, including tags with various pre-printed indicia, tags with fastening means carried on their rear or mounting surfaces, and tags having purposeful areas for auxiliary markings to be added by the user, but no tags of the conveniently and releasably permanent nature of the present kit have been provided, nor them in a kit with a panel member providing both an attachment surface and a orderly-arrangement spacer for a group of tubes or lines;

d. The prior art for many years has had body members which serve as terminal blocks for a plurality of associated lines, which are separated although adjacent on the mount.

e. The prior art for many years has fastened objects in space adjacency on other mounts, in many and quite varied situations, such as point-of-sale merchandising practices, hanging clothes on a line for drying, signboards with attachable letters, etc.

f. The prior art for many years has known of a great need for identifying lines or conduits and has used various identification procedures, such as by using lines of different colors or different color-patterns, and even identifying by some sort of identification tag or tags, etc.

Thus, the prior art in various fields is not only acknowledged, it is emphasized, for it helps to show by its very diversity that although the prior art has had all types of line-identifications, and has had knowledge of various identification and mounting concepts and details for many years, and with such worldwise knowledge by indefinite numbers of persons throughout those years, and in spite particularly of problems of identifying individual ones of a plurality of tubes in medical uses and particularly medical uses involving a plurality of similar-appearing tubes as servicing a patient by greatly differing liquids, none of the prior art has provided nor suggested the simplified and overall concepts which characterize the combination of the present invention, and by which this invention has been achieved; and more particularly, none of the prior art has suggested or achieved the particular concepts of advantageous combination considered as a kit, as provided by the present invention, with the advantageous construction and ease of operation concepts and characteristics of the present invention.

Accordingly, the various concepts and components are conceded and emphasized to have been widely known in the prior art; nevertheless, the prior art not having had the present concepts in a kit-form combination to achieve the overall invention as a whole, even only a fair amount of realistic humility, to avoid consideration of this invention improperly by hindsight, requires the concepts and achievements here of the combination shown herein to be realistically viewed as inventive in their nature. And especially is this a realistic consideration when viewed from the position of a person of ordinary skill in this art at the time of this invention, and without trying to reconstruct this invention from the prior art without use of hindsight toward particulars not suggested by the prior art of all relevant fields.

BRIEF DESCRIPTION OF THE DRAWINGS

The above description of the novel and advantageous invention is of somewhat introductory and generalized form. More particular details, concepts, and features are set forth in the following and more detailed description of an illustrative embodiment, taken in conjunction with the accompanying drawings, which are of somewhat schematic and diagrammatic nature, for showing the inventive concepts; and in the drawings:

FIGS. 1 and 2 are pictorial illustrations of the invention in typical use, with a few I.V. tubes attached to a patient and extending from the patient to associated equipment or supports such as a so-called I.V. Pole in FIG. 2, and both FIGS. 1 and 2 illustrating particularly the orderliness and ease of identification of the tubing lines as achieved by the identification straps holding the I.V. tubes onto the invention's main body member in an arrangement of orderly spacing; and, more particularly:

FIG. 1 shows the body member attached around the patient's arm; and

FIG. 2 shows the body member attached body member attached around the cot headboard, illustratively of attachment of the body member being attached to any portion of the cot or bedding items;

FIG. 3, in much larger scale, illustrates an elevation view of the invention's base panel or body member, with various ones of the I.V. lines being held thereto by the kit of identification's support straps or tags;

FIG. 4 is a detail cross-sectional view, of so-called "broken section" nature, generally as taken by Section-line 4—4 of FIG. 3;

FIG. 5 is a detail view, generally shown as would be seen by View-line 5—5 of FIG. 3;

FIG. 6 is an enlarged detail of a portion of FIG. 5, for clarity of reference numeral lead-lines; and FIG. 7 is a pictorial illustration, similar to FIG. 2 but on a larger scale, showing the invention i a typical use in identifying and keeping in an orderly arrangement a plurality of I.V. tubes connected to a patient on a mobile cot, and with the main body member of the kit affixed to the sheeting of the cot.

DETAILED DESCRIPTION OF PREFERRED EMBODIMENT

As shown in the drawings, the preferred embodiment of the invention provided as a kit, providing, when the parts are co-operatively used as herein detailed, an identification accessory drive 10 providing for the individual or pluralistic labelling of a set of slender work objects 12, and an organizer for orderliness of each one of a set of those objects; and use with tubes 12 attached to adjacent equipment such as a so-called intravenous infusion pole ("I.V. pole"), four lines 12 being shown illustratively of the use, may be considered as a typical use for the device 10.

In the particular use primarily contemplated by the inventors, the work objects are the various lines of tubing in situations of medical therapy, each of the tubes 12 containing a particular fluid useful in treating, monitoring, or otherwise servicing a patient; and although the concepts are not limited to use in medical therapy, or even medical situations in general, the work objects 12 are contemplated to be operatively flexible or otherwise accommodative of shifting of their locations so as to advantageously receive not only the identification effect but the effect of orderly arrangeability, i.e., to be positionable in spaced although adjacent relation to one another when the kit is used for a plurality of work objects or tubing 12.

The kit is quite simple from standpoints of mechanics, economy, and convenience and ease of use, economically consisting of two general components, i.e., in the embodiment shown, just a single body member 14 of a panel-like form, and a set of strap-like identification bodies or tags 16. The relative sizes of the panel body 14 and tags 16 are such that an appropriate number of the tags 16, for the tubes 12 of the work-situation involved for use of the kit, may be mounted on the body member 14 without interference.

Ease of use of the panel 14 and the straps of tags 16 is achieved in the preferred embodiment by a first Velcro-nature fastener surface means 18 being carried on the outer surface 20 of the body member 14, and the set of identification bodies 16 are each provided with a second co-operative type Velcro-nature fastener means 22 on their rear surface 24.

The tags or straps 16 carry, respectively, various identification indicia 26 appropriate for the respective tubing liens 12; and in the form shown, the indicia 26 are provided by being printed onto the outer surface 28 of the tags 16, as to tags 16 for use with known or predictable tubings 12, but on some tags 16 area 30 is left open for on-site marking.

The identification bodies 16 are conveniently usable, for each is engageable with both a respective work object 12 and with the body member 14's fastener surface means 18, with the identification indicia 26 showing outwardly, and also supportively holding the respective work object 12 to the body member 14; and with the tags 16 in the form of small flexible straps, and with their Velcro fastener surface 22 on at least the opposite outer portions 32 of their rear surfaces 24, that holding of the respective tubing line 12 is readily and easily achieved by placing the tag 16 with its central area 33 over the tubing 12, and merely pressing the tag's spaced end-portions 32 onto the Velcro fastener surface 18 of the panel member 14.

Advantageously, the arrangement provides that each of the work objects 12 will be both labelled by respective identification bodies 16 and the work objects 12 will be held orderly, in adjacently spaced relation against the body member 14 with the identification tag bodies 16 providing the double function of holding the work objects 12 to the body member 14 and providing identification of the respective work objects 12. Moreover, the body member 14 provides the double function of retaining the identification bodies 16 and providing a support for the supported arrangement of the work objects 12 in that orderly, adjacently-spaced manner.

The basic kit as described above, comprising a panel body 14 and a set of tags 16, is also desirably provided with the additional and releasable support strap 34, which provides means for supporting the panel body 14 if it is desired to support the panel 14 other than by its being supported by the tubing lines 12 attached to it by the tag straps 16.

In the kit using a separate support strap 34, as shown, the rear surface 36 of the panel body member 14 is provided with first type Velcro-nature surface means 38; and the support strap 34 is provided to have on its forward side 40 a second or co-operative type Velcro-nature surface means 42 and on its rearward side 44 an adhesive means 46. This adhesive surface 46, if the extra strap 34 is used, provides means of easy attachment of the panel body 14 to an associated wall or other support surface if desired, by removing a layer of protective paper 48 covering the adhesive layer 46. Such support surface depends on what is handy, e.g., the cot's headboard 50 (FIG. 2) or sheeting 52 (FIG. 7).

In the form shown the Velcro-nature outer surface means 18 of the panel body 14 is carried on the outer surface 20 of the body member 14 by being stitched thereto as indicated diagrammatically at 53; and, not needing much rigidity in use, the body member 14 is provided as a flexible strap of a soft nature accommodating a stitching procedure.

Desirably as shown, the panel member 14 may be formed of actually two layers 54 and 56, each carrying respectively Velcro areas 18 and 38, depending on the availability of Velcro sheeting; and by providing the panel member 14 of the two layers 54 and 56, each can be obtained with Velcro areas 18 or 38 already attached to the respective layer 54 or 56 without trying to locate a source of Velcro sheeting having Velcro on both sides, or try to attach Velcro on both sides by a single stitching operation.

It is also desired, as shown in FIG. 3, to have a peripheral portion of the panel 14 (outer layer 54) extend outward of the Velcro area 18, providing a non-Velcro border portion 58 which is both attractive and provides for convenient grab of the tags 16 when pulling them off the panel 14's Velcro 18.

The use of the kit is easy and convenient in all respects of both attaching and removing the tags 16 for innumerable repetitions of uses; and, as shown, with the first type Velcro-nature outer surface means 18 provided over substantially the entire surface span 20 of the body member 14 there is avoided for the user any need of strict precision of placement of individual identification bodies 16 for attaining a substantially orderly arrangement of the plurality of tubing lines 12.

We claim:

1. An identification accessory device providing for pluralistic labelling of an associated set of slender work objects which are operatively accommodative of shifting of their locations so as to be positionable in spaced although adjacent relation to one another, the device comprising:
    a body member;
    the body member having an outer surface on which is carried a first type Velcro-nature fastener means;
    a set of identification bodies each having a rear surface, and provided with a second-type Velcro-nature fastener means on their rear surface, and carrying an identification indicia;
    the identification bodies being respectively engageable with both the associated work objects and with the body member's outer surface, with the identification indicia showing outwardly, and supportively holding the associated work objects to the body member;
    the fastener means on the outer surface of the body member, and on the rear surface of each identification body, both extending over the location of the axis of the work object, permitting freedom of movement of the work object in a direction longitudinal of itself, but extending so close to the object axis as to substantially prevent movement transverse to said axis even though not having any adhesion contact with the object;
    the arrangement providing that each of the associated work objects will be both labelled by respective identification bodies, and the work objects will be held in adjacently spaced relation against the body member, with the identification bodies providing the double function of holding the work objects to the body member and providing identification of the respective work objects, and the body member providing the double function of retaining the identification bodies and providing a support for the supported arrangement of the work objects in an adjacently spaced manner;
    in which the body member has a rear surface which is provided with a first type Velcro-nature surface means,
    a support strap being provided having on one side a second type Velcro-nature surface means and on the other side of an adhesive means.

2. The invention as set forth in claim 1 in a combination in which the first type Velcro-nature outer surface means is carried on the outer surface of the body member by being stitched thereto.

3. The invention as set forth in claim 1 in a combination in which the body member is provided as a flexible strap.

4. The invention as set forth in claim 1 in a combination in which the identification bodies are flexible, accommodating their being manually bent over a respective work object and caused to adhere to the outer Velcro means surface of the body member.

5. The invention as set forth in claim 1 in a combination in which the identification bodies are provided with spaced Velcro areas, accommodating the Velcro fastening of spaced regions of the identification body to the body member on each side of a respective work object.

6. The invention as set forth in claim 1 in a combination in which the first type Velcro-nature outer surface means is provided over substantially the entire span of the body member, thus avoiding for the user any need of strict precision of placement of individual identification bodies for a substantially orderly arrangement thereof.

7. An identification accessory device providing for pluralistic labelling of an associated set of slender work objects which are operatively accommodative of shifting of their locations so as to be positionable in spaced although adjacent relation to one another, the device comprising:
    a body member;
    the body member having an outer surface on which is carried a first type Velcro-nature fastener means;
    a set of identification bodies each having a rear surface, and provided with a second-type Velcro-nature fastener means on their rear surface, and carrying an identification indicia;

the identification bodies being respectively engageable with both the associated work objects and with the body member's outer surface, with the identification indicia showing outwardly, and supportively holding the associated work objects to the body member;

the fastener means on the outer surface of the body member, and on the rear surface of each identification body, both extending over the location of the axis of the work object, permitting freedom of movement of the work object in a direction longitudinal of itself, but extending so close to the object axis as to substantially prevent movement transverse to said axis even though not having any adhesion contact with the object;

the arrangement providing that each of the associated work objects will be both labelled by respective identification bodies, and the work objects will be held in adjacently spaced relation against the body member, with the identification bodies providing the double function of holding the work objects to the body member and providing identification of the respective work objects, and the body member providing the double function of retaining the identification bodies and providing a support for the supported arrangement of the work objects in an adjacently spaced manner;

in which the body member has a rear surface which is provided with a first type Velcro-nature surface means, a support strap being provided having on one side a second type Velcro-nature surface means and on the other side an adhesive means, in which the identification bodies are provided as straps.

* * * * *